(12) United States Patent
Jun et al.

(10) Patent No.: US 6,740,783 B1
(45) Date of Patent: May 25, 2004

(54) PROCESS FOR PREPARING DIMETHYL ETHER FROM CRUDE METHANOL

(75) Inventors: Ki-Won Jun, Daejeon (KR); Hyun-Seog Roh, Daejeon (KR); Kew Ho Lee, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 10/413,535

(22) Filed: Apr. 15, 2003

(30) Foreign Application Priority Data

Dec. 11, 2002 (KR) ................. 10-2002-0078856

(51) Int. Cl.$^7$ ............................................. C07C 41/09
(52) U.S. Cl. ....................................................... 568/698
(58) Field of Search ......................................... 568/698

(56) References Cited

U.S. PATENT DOCUMENTS

| | | | | |
|---|---|---|---|---|
| 3,036,134 A | * | 5/1962 | Mattox ...................... | 568/698 |
| 4,845,063 A | * | 7/1989 | Chu ........................... | 502/60 |
| 5,684,213 A | * | 11/1997 | Nemphos et al. .......... | 568/698 |

FOREIGN PATENT DOCUMENTS

| JP | 59-16845 | 1/1984 |
|---|---|---|
| JP | 59-42333 | 3/1984 |

\* cited by examiner

*Primary Examiner*—Rosalynd Keys
(74) *Attorney, Agent, or Firm*—McGuire Woods LLP

(57) ABSTRACT

The present invention relates to a process for preparing dimethyl ether from crude methanol. More particularly, this invention relates to an improved process for preparing dimethyl ether useful as a fresh fuel as well as a raw material in chemical industry with no generation of hydrocarbon as a by-product and no deactivation of a catalyst, performed in such a manner that the dehydration is carried out using as raw material crude methanol that contains water in the presence of the zeolite catalyst represented by the following formula (I), wherein hydrogen cations (H$^+$) of hydrophobic zeolite in said zeolite catalyst are partially replaced with certain metal ions or ammonium ions:

$$H_xM_{(1-x)/n}Z \qquad (I)$$

wherein H represents a hydrogen cation; M represents one or more cations selected from the group consisting of metal ions of IA Group, IIA Group, IB Group and IIB Group in Periodic Table and ammonium ions; n represents oxidation number of substituted cation (M); x represents mole % ranging from 10 to 90 based on the amount of hydrogen cations; and Z represehts a hydrophobic zeolite having the SiO$_2$/Al$_2$ O$_3$ ratio of 20–200.

3 Claims, No Drawings

PROCESS FOR PREPARING DIMETHYL ETHER FROM CRUDE METHANOL

BACKGROUND OF THE INVENTION

1. Field of the Invention

The present invention relates to a process for preparing dimethyl ether from crude methanol. More particularly, this invention relates to an improved process for preparing dimethyl ether useful as a clean fuel as well as a raw material in chemical industry with no generation of hydrocarbon as a by-product and no deactivation of a catalyst, performed in such a manner that the dehydration is carried out using as a raw material crude methanol that contains water in the presence of the zeolite catalyst represented by the following formula (I), wherein hydrogen cations (H$^+$) of hydrophobic zeolite in said zeolite catalyst are partially replaced with certain metal ions or ammonium ions:

$$H_xM_{(1-x)/n}Z \quad (I)$$

wherein H represents a hydrogen cation; M represents one or more cations selected from the group consisting of metal ions of IA Group, IIA Group, IB Group and IIB Group in Periodic Table and ammonium ions; n represents oxidation number of substituted cation (M); x represents mole % ranging from 10 to 90 based on the amount of hydrogen cations; and Z represents a hydrophobic zeolite having the $SiO_2/Al_2O_3$ ratio of 20–200.

2. Description of the Related Art

Dimethyl ether has been used as a principal material with its high applicability in chemical industry such as an aerosol propellant and as a clean fuel. Considering the high likelihood of dimethyl ether to replace the conventional fuels that have been used for internal combustion engines, there is a need for the development of a more economic process for its preparation.

Most processes for preparing dimethyl ether performed in industrial scale are carried out through the dehydration of methanol represented by the following reaction Scheme I:

$$2CH_3OH \rightarrow CH_3OCH_3 + H_2O \quad (I)$$

The preparation process of dimethyl ether through dehydration of methanol is performed at a temperature of 250–450° C. and frequently uses a solid acid catalyst. The solid acid catalyst useful in the process for preparing dimethyl ether includes gamma-alumina (Japanese Patent Kokai 1984-16845), silica-alumina (Japanese Patent Kokai 1984-42333) and so on. However, gamma-alumina and silica-alumina are both hydrophilic and thus it is very likely that water can adsorb to their surfaces, which results in lowering their activation site thereby decreasing their catalytic activities. Therefore, the activity of a solid acid catalyst is significantly decreased when the methanol, which is used as a raw material in the process for preparing dimethyl ether, contains water. For this reason, the methanol whose water content has been customarily decreased to the level of below a few hundreds ppm to be used for preparing dimethyl ether. However, the methanol produced as a synthetic gas generally contains 10–20% of water as a by-product and thus the complete removal of water by distillation is required. In addition, unreacted methanol recovered and reused in the process of dimethyl ether preparation contains relatively large amount of water generated in dehydration step and thus there needs an additional step of distillation to remove the water.

It is understood to one skilled in the art that a novel catalyst not liable to be deactivated by water may be able to drastically reduce the energy consumption in distillation step of dimethyl ether preparatiion, which may result in considerable cost and time effectiveness as compared to the existing processes.

Since the reaction of converting methanol to dimethyl ether is proceeded by means of an acid catalyst and the production of dimethyl ether corresponds to an intermediate generated in the course of production of hydrocarbon, the acid site strength of an acid catalyst is responsible for its activity and selectivity. For example, in the presence of a catalyst which carries a strong acid site, methanol is converted to dimethyl ether and an additional reaction is followed to produce hydrocarbon as a by-product; in contrast, in the presence of a catalyst which carries a weak acid site, the conversion of methanol to dimethyl ether is not possible due to low activity of the catalyst.

Examples of acid catalysts that are resistant to water adsorption are a hydrophobic zeolite such as USY, Mordenite, ZSM-type and Beta. Such zeolite generates hydrocarbon and coke through a side reaction because of their strong acid sites while producing dimethyl ether from methanol, which then results in lowering their selectivities. According to the researches of the present inventors, the general H-USY, H-ZSM-5 and H-Beta zeolites are disadvantageous in that the by-products of hydrocarbon such as methane, ethane and propane are formed due to strong acid sites of their zeolites. The hydrocarbons generated as by-products are alkanes with low molecular weight and have a very low value as a product and also deactivate the catalyst through coking.

SUMMARY OF THE INVENTION

The present inventors have conducted intensive researches to develop a novel catalyst which is not easily deactivated by water in the process of dimethyl ether preparation via methanol dehydration. As a result, the inventors found that hydrophobic zeolites serving as a catalyst such as USY, Mordenite, ZSM-type and Beta provide a high catalytic activity for a long period of time without deactivating the catalyst by water; in addition, it has been discovered that the above-indicated hydrophobic zeolites whose hydrogen cations are partially replaced with suitable metal ions or ammonium ions so as to remove too strong acid sites exhibit relatively high catalytic activities and prevent the generation of hydrocarbon as a by-product, thereby dramatically improving the yield of dimethyl ether. Moreover, the present inventors have found when crude methanol that contains water is used as a raw material, the strong Lewis acid sites in the zeolite catalyst is more or less deactivated by water, which prevents the generation of hydrocarbon as a by-product and a coking phenomenon.

Accordingly, it is an object of this invention to provide a process for preparing dimethyl ether with an improved yield by use of crude methanol that contains wateras a raw material.

DETAILED DESCRIPTION OF THE INVENTION

In an aspect of this invention, there is provided a process for a dimethyl ether comprising (a) a partial substitution of hydrogen cations of a hydrophobic zeolite and (b) dehydration of crude methanol that contains water in the presence of a hydrophobic zeolite catalyst represented by the following formula (I) containing said hydrophobic zeolite:

$$H_xM_{(1-x)/n}Z \quad (I)$$

wherein H represents a hydrogen cation; M represents one or more cations selected from the group consisting of metal ions of IA Group, IIA Group, IB Group and IIB Group in Periodic Table and ammonium ions; n represents an oxidation number of substituted cations (M); x represents a mole % ranging from 10 to 90 based on the amount of hydrogen cations; and Z represents a hydrophobic zeolite with the $SiO_2/Al_2O_3$ ratio of 20–200.

The present invention will be described in more detail hereunder:

The present invention is directed to a novel use of a catalyst represented by the formula (I) as the catalyst useful in preparing dimethyl ether by methanol dehydration.

Since the catalyst of the formula (I) is capable of maintaining catalytic activity for a long period of time without deactivating the catalyst by water, it performs effectively the methanol dehydration even when crude methanol that contains water is used as a raw material. In addition, the hydrophobic zeolite catalyst of the formula (I) can completely prevent the generation of hydrocarbon and coke so that the selectivity of dimethyl ether is noticeably improved, because a portion of hydrogen cations in the catalyst are suitably replaced with other cations to remove strong acid sites, which then suppress side reactions.

Therefore, according to the present process, the crude methanol that contains water discharged from a variety of processes can be used as per se, which manifests significantly the advantages of the catalyst of the formula (I). The effectiveness of the present catalyst is maximally exhibited when the crude methanol containing 5–50 mole % of water is used.

In the catalyst of the formula (I) employed in the methanol dehydration of the present invention, the zeolite (Z) is a hydrophobic one including USY, Mordenite, ZSM typed, Beta and the like. It is suitable that the ratio of $SiO_2/Al_2O_3$ in the zeolite is 20–200: if the ratio is less than 20, the zeolite becomes hydrophilic so that it can more readily adsorb to water to deactivate the catalyst; to the contrary, if the ratio is more than 200, the amount of acid site is negligible so that the methanol dehydration may not be effectively elicited. In addition, according to the present invention, for adjusting the strength of the strong acid site suitably, the hydrogen cations of the zeolite catalyst are ion-exchanged with at least one cation selected from the group consisting of ions of IA Group (alkali metal), IIA Group (alkaline earth metal), IB Group (e.g., Cu, Ag, etc.) and IIB Group (e.g., Zn, etc.) and ammonium ions within the extent that the content of the hydrogen cation is maintained to be 10–90 mole %.

The examples of conventional zeolites commonly used are a Na type zeolite with ion-exchanged Na+(e.g, Na-ZSM-5, Na-Beta, Na-MOR, etc.) and a H type zeolite with ion-exchanged H+(e.g., H-ZSM-5, H-Beta, H-MOR, etc.). However, according to the investigation of the present inventors, the Na type zeolite carrying solely weak acid sites is not effective in the present process, and the H type zeolite with ion-exchanged H+ carrying too strong acid sites generates hydrocarbon as a by-product. In contrast, the catalyst employed in this invention has the content of the hydrogen cation from 10 to 90 mole %, which is a suitable acid site range for the production of dimethyl ether.

As such, the present invention can prevent completely both the deactivation of the catalyst that occurs in the conventional process for preparing dimethyl ether and the generation of hydrocarbon as a by-product, thereby dramatically improving the yield of dimethyl ether.

The manufacturing method of the catalyst represented by the formula (I) described above will be described in more detail as follows.

In the present invention, an ion-exchange method by using metal ions was selected to adjust the strength of strong acid sites of the hydrophobic catalyst whose $SiO_2/Al_2O_3$ ratio ranges from 20 to 200. For example, in preparing a NaH type zeolite, $NH_4$ type zeolite is ion-exchanged in a salt aqueous solution containing sodium such as sodium chloride and sodium nitrate, dried and calcined. In addition, in preparing a CuH type zeolite, a $NH_4$ type zeolite is ion-exchanged in a salt aqueous solution containing copper such as copper chloride and copper nitrate, dried and calcined. In manufacturing a ZnH type zeolite, a $NH_4$ type zeolite is ion-exchanged in salt aqueous solution containing zinc such as zinc chloride and zinc nitrate, dried and calcined. When the above preparation process is carried out, the strength of acid site in the hydrophobic catalyst including USY, Mordenite, ZSM type, Beta and the like whose $SiO_2/Al_2O_3$ ratio ranges from 20 to 200 is determined depending on the ion exchange amount. In order to prepare the zeolite catalyst carrying the strong acid sites suitable for the present invention, it is preferred that the mole ratio of the hydrogen cations ranges from 10 to 90 mole %.

The general process for preparing dimethyl ether by methanol dehydration, which is performed in the presence of the hydrophobic zeolite catalyst represented by the formula (I) and prepared according to the process aforementioned, will be described as follows: The catalyst represented by the formula (I) is charged into a reactor and then pretreated prior to methanol dehydration. The pretreatment is accomplished in such a manner that an inert gas such as nitrogen is passed at a temperature of 200–350° C. and a flow rate of 20–100 ml/g-catalyst/min. The methanol is contacted to the pretreated catalyst bed of the reactor. Here, the reaction temperature shall be maintained at 150–350° C. If it is below 150° C., the reaction rate becomes insufficient thus lowering the conversion rate; and if it is above 350° C., the generation of dimethyl ether is unfavorable in view of thermodynamics thus lowering the conversion rate. In addition, the reaction pressure shall be maintained at 1–100 atm. If it is higher than 100 atm, the productivity of the reaction becomes poor. As to LHSV (Liquid hourly space velocity), it is preferred that the methanol dehydration be executed in the range of 0.05–50 h$^{-1}$ based on absolute methanol. If LHSV is less than 0.05 h$^{-1}$, the productivity of the reaction becomes extremely poor, whereas the conversion is decreased due to the shortened contact time with a catalyst if it is higher than 50 h$^{-1}$. The reactors suitable in the present process include a fixed bed reactor, a fluidized-bed reactor with gas phase, and a slurry reactor with liquid phase, and they exhibit similar effects.

As described hereinabove, the present invention uses a zeolite catalyst with adjusted strong acid sites, which can prevent the deactivation of the catalyst even when using crude methanol as a raw material containing 5–50 mole % of water and can avoid the generation of hydrocarbon as a by-product, whereby dramatically improving the yield of dimethyl ether.

The following specific examples are intended to be illustrative of the invention and should not be construed as limiting the scope of the invention.

EXAMPLE 1

$NH_4$-ZSM-5($SiO_2/Al_2O_3$=30) zeolite was added to 100 ml of 0.1 N NaCl solution, agitated for 24 hours at 80° C., filtered, washed with distilled water and dried for 12 hours at 120° C., followed by calcination for 12 hours at 500° C. to yield NaH-ZSM-5(Na ion exchange rate=44 mole %). The NaH type zeolite thus yielded was molded into a size of 60–80 meshes in pelletizer, 2.5 ml of it was collected and charged into a fixed bed reactor. Then, nitrogen gas was flowed into the reactor at a rate of 50 ml/min and the temperature of the reactor was adjusted to 270° C. The methanol containing 30 mole % of water was passed into the catalyst bed at the rate of LHSV of 5.5 $h^{-1}$ wherein the reactor is kept at 270° C. with a pressure of 1 atm. The results are shown in Table I.

EXAMPLE 2

The catalyst used was prepared same as in Example 1 except that 0.5 N NaCl solution was used for NaH type ZSM-5 preparation (Na ion exchange rate=78 mole %). Then, the methanol dehydration was carried out as in Example 1. The results are shown in Table I.

EXAMPLE 3

$NH_4$-Beta zeolite was added to 100 ml of 1 N NaCl solution, agitated for 24 hours at 80° C., filtered, washed with distilled water and dried for 12 hours at 120° C. The resultant was again added to 100 ml of 1 N NaCl solution, ion-exchanged, filtered, washed and dried as the above procedures, followed by calcination for 12 hours at 500° C. to yield NaH type Beta zeolite (Na ion exchange rate=88 mole %).

Then, the methanol dehydration was carried out as in Example 1. The results are shown in Table I.

EXAMPLE 4

$NH_4$-MOR(Mordenite) zeolite was added to 100 ml of 0.5 N copper nitrate solution, agitated for 24 hours at 80° C., filtered, washed with distilled water and dried for 12 hours at 120° C. The resultant was again added to 100 ml of 0.5 N copper nitrate solution, ion-exchanged, filtered, washed and dried as the above procedures, followed by calcination for 12 hours at 500° C. to yield CuH typed MOR zeolite (Cu ion exchange rate=72 mole %).

Then, the methanol dehydration was carried out as in Example 1. The results are shown in Table I.

EXAMPLE 5

$NH_4$-USY zeolite was added to 100 ml of 0.5 N zinc nitrate solution, agitated for 24 hours at 80° C., filtered, washed with distilled water and dried for 12 hours at 120° C. The resultant was again added to 100 ml of 0.5 N zinc nitrate solution, ion-exchanged, filtered, washed and dried as the above procedures, followed by calcination for 12 hours at 500° C. to yield ZnH-USY zeolite (Zn ion exchange rate=70 mole %).

Then, the methanol dehydration was carried out as in Example 1. The results are shown in Table I.

EXAMPLE 6

$NH_4$-ZSM-5 zeolite was added to 100 ml of 0.5 N copper nitrate solution, agitated for 24 hours at 80° C., filtered, washed with distilled water and dried for 12 hours at 120° C. The resultant was again added to 100 ml of 0.5 N copper nitrate solution, ion-exchanged, filtered, washed and dried as the above procedures, followed by calcination for 12 hours at 500° C. to yield CuH typed ZSM-5 zeolite (Cu ion exchange rate=80 mole %).

Then, the methanol dehydration was carried out as in Example 1. The results are shown in Table I.

EXAMPLE 7

$NH_4$-Beta zeolite was added to 100 ml of 0.5 N zinc nitrate solution, agitated for 24 hours at 80° C., filtered, washed with distilled water and dried for 12 hours at 120° C. The resultant was again added to 100 ml of 0.5 N zinc nitrate solution, ion-exchanged, filtered, washed and dried as the above procedures, followed by calcination for 12 hours at 500° C. to yield ZnH typed Beta-zeolite (Zn ion exchange rate=73 mole %).

Then, the methanol dehydration was carried out as in Example 1. The results are shown in Table I.

EXAMPLE 8

H-ZSM-5($SiO_2/Al_2O_3$=30) zeolite was added to 100 ml of 0.1 N ammonium nitrate solution, agitated for 24 hours at 80° C., filtered, washed with distilled water and dried for 12 hours at 120° C., followed by calcination for 12 hours at 300° C. to yield $NH_4$H-ZSM-5($NH_4$ ion exchange rate=57 mole %).

Then, the methanol dehydration was carried out as in Example 1. The results are shown in Table I.

EXAMPLE 9

The preparation of catalyst and methanol dehydration was carried out as in Example 1, except that methanol dehydration was performed at 250° C. The results are shown in Table I.

EXAMPLE 10

The preparation of catalyst and methanol dehydration was carried out as in Example 1, except that the LHSV for methanol dehydration was 7 $h^{-1}$. The results are shown in Table I.

EXAMPLE 11

The preparation of catalyst and methanol dehydration was carried out as in Example 1, except that the temperature and LHSV for methanol dehydration were 250° C. and 7 $h^{-1}$, respectively. The results are shown in Table I.

EXAMPLE 12

The preparation of catalyst and methanol dehydration was carried out as in Example 1, except that the methanol containing 10 mole % water was passed into catalyst bed at a space velocity of LHSV 5.5 $h^{-1}$. The results are shown in Table II.

EXAMPLE 13

The preparation of catalyst and methanol dehydration was carried out as in Example 1, except that the methanol containing 20 mole % water was passed into catalyst bed at a space velocity of LHSV 5.5 $h^{-1}$. The results are shown in Table II.

EXAMPLE 14

The preparation of catalyst and methanol dehydration was carried out as in Example 1, except that the methanol containing 40 mole % water was passed into catalyst bed at a space velocity of LHSV 5.5 $h^{-1}$. The results are shown in Table II.

COMPARATIVE EXAMPLE 1

The gamma-alumina catalyst was molded into a size of 60–80 meshes in a pelletizer, and then 2.5 ml of it was collected and charged into a fixed bed reactor. Then, nitrogen gas was flowed into the reactor at a rate of 50 ml/min and the temperature of the reactor was adjusted to 270° C. The methanol containing 30 mole % of water was passed into the catalyst bed at the rate of LHSV of 5.5 h$^{-1}$ wherein the reactor is kept at 270° C. with a pressure of 1 atm while simultaneously measuring the reaction activity. The results are shown in Table I.

COMPARATIVE EXAMPLE 2

The silica-alumina($Al_2O_3$=14 wt %) catalyst was molded into a size of 60–80 meshes in pelletizer, 2.5 ml of it was taken and charged into a fixed bed reactor. Then, nitrogen gas was flowed into the reactor at a rate of 50 ml/min and the temperature of the reactor was adjusted to 270° C. The methanol containing 30 mole % of water was passed into the catalyst bed at the rate of LHSV of 5.5 h$^{-1}$ wherein the reactor is kept at 270° C. with a pressure of 1 atm while simultaneously measuring the reaction activity. The results are shown in Table I.

COMPARATIVE EXAMPLE 3

Using Na-ZSM-5 zeolite, the reactions were carried out as described in Example 1. The results are shown in Table I.

COMPARATIVE EXAMPLE 4

Using Na-Beta zeolite, the reactions were carried out as described in Example 1. The results are shown in Table I.

COMPARATIVE EXAMPLE 5

Using HZSM-5 zeolite, the reactions were carried out as described in Example 1. The results are shown in Table I.

COMPARATIVE EXAMPLE 6

Using H-Beta zeolite, the reactions were carried out as described in Example 1. The results are shown in Table I.

Table I shows the results of methanol dehydration performed by using a catalyst prepared in Examples 1–10 and Comparative Examples 1–5, respectively, and by using the methanol containing 30 mole % of water as a starting material under the same condition.

TABLE I

| Example | Catalyst | Hydrogen cation(mole %) | Yield (%) Dimethyl ether | Yield (%) Hydrocarbon |
|---|---|---|---|---|
| Exam. 1 | NaHZSM-5 | 56 | 80.5 | 0.0 |
| Exam. 2 | NaHZSM-5 | 22 | 80.4 | 0.0 |
| Exam. 3 | NaHBeta | 12 | 75.3 | 0.0 |
| Exam. 4 | CuHMor | 28 | 78.1 | 0.0 |
| Exam. 5 | ZnHUSY | 30 | 68.3 | 0.0 |
| Exam. 6 | CuHZSM-5 | 20 | 80.4 | 0.0 |
| Exam. 7 | ZnHBeta | 27 | 76.2 | 0.0 |
| Exam. 8 | NH$_4$HZSM-5 | 43 | 78.7 | 0.0 |
| Exam. 9 | NaHZSM-5 | 56 | 72.7 | 0.0 |
| Exam. 10 | NaHZSM-5 | 56 | 75.4 | 0.0 |
| Exam. 11 | NaHZSM-5 | 56 | 70.4 | 0.0 |
| Com.Exam. 1 | Gamma-alumina | — | 48.0 | 0.0 |
| Com.Exam. 2 | Silica-alumina | 0 | 37.3 | 0.0 |
| Com.Exam. 3 | NaZSM-5 | 0 | 0.0 | 0.0 |

TABLE I-continued

| Example | Catalyst | Hydrogen cation(mole %) | Yield (%) Dimethyl ether | Yield (%) Hydrocarbon |
|---|---|---|---|---|
| Com.Exam. 4 | NaBeta | 0 | 0.0 | 0.0 |
| Com.Exam. 5 | HZSM-5 | 100 | 78.1 | 2.1 |
| Com.Exam. 6 | HBeta | 100 | 74.2 | 1.8 |

As indicated in Table I, the methanol dehydration using the catalyst of the present invention showed a higher yield of dimethyl ether and also generated no hydrocarbon as a by-product. In contrast, when the methanol dehydration was performed by using the gamma-alumina catalyst, conventionally used in the industry, and using methanol containing 30 mole % water as a raw material, the catalyst was deactivated to show lower yield of dimethyl ether (48%) (Comparative Example 1). Where the silica-alumina was used as a catalyst, the yield of dimethyl ether (37%) was exhibited to be lower than that when used the gamma-alumina. Moreover, when NaZSM-5 and NaBeta zeolite were used (Comparative Examples 3 and 4), the catalytic activities were not completely manifested. In addition, the H type zeolite carrying strong acid site (Comparative Examples 5 and 6) generated hydrocarbon as a by-product while showing a high yield of dimethyl ether. The hydrocarbons formed as a by-product are alkanes with low molecular weight and have a negligible value as a product, leading to the deactivation of catalyst through the generation of carbon.

Table II summarizes the results of methanol dehydration using NaHZSM-5 catalyst prepared in Example 1 and crude methanol as a starting material that contains different amount of water, performed under the same condition.

TABLE II

| Examples | Content of water in methanol (mole %) | Yield (%) Dimethyl ether | Yield (%) Hydrocarbon |
|---|---|---|---|
| Exam.12 | 10 | 68.5 | 0.0 |
| Exam.13 | 20 | 78.1 | 0.0 |
| Exam.14 | 40 | 63.3 | 0.0 |

As shown in Table II, the present catalyst exhibited a higher yield of dimethyl ether even when crude methanol contained 10–40 mole % of water, and no hydrocarbon was produced as a by-product.

As described hereinabove, when dimethyl ether is prepared from methanol using a hydrophobic zeolite catalyst including USY, Mordenite ZSM typed, Beta and the like where acid sites are adjusted, the improvement in yield of dimethyl ether was significant due to higher catalytic activity while preventing the generation of hydrocarbon as a by-product.

What is claimed is:

1. A process for preparing dimethyl ether comprising
   (a) a partial substitution of hydrogen cations of a hydrophobic zeolite and
   (b) dehydration of crude methanol that contains water in the presence of a hydrophobic zeolite catalyst represented by the following formula (I) containing said hydrophobic zeolite:

 (I)

wherein H represents a hydrogen cation; M represents one or more cations selected from the group consisting of metal ions of IA Group, IIA Group, IB Group and IIB Group in Periodic Table and ammonium ions; n represents an oxidation number of substituted cations (M); x represents a mole % ranging from 10 to 90 based on the amount of hydrogen cations; and Z represents a hydrophobic zeolite with the $SiO_2/Al_2O_3$ ratio of 20–200.

2. The process according to claim 1, wherein said crude methanol contains 5–50 mole % of water.

3. The process according to claim 1, wherein said dehydration is performed under the conditions of a reaction temperature of 150–350° C., a reaction pressure of 1–100 atmosphere and LHSV (liquid hourly space velocity) of 0.05–50 $h^{-1}$.

* * * * *

UNITED STATES PATENT AND TRADEMARK OFFICE
CERTIFICATE OF CORRECTION

PATENT NO. : 6,740,783 B1
DATED : May 25, 2004
INVENTOR(S) : Ki-Won Jun et al.

It is certified that error appears in the above-identified patent and that said Letters Patent is hereby corrected as shown below:

<u>Title page,</u>
Item [57], ABSTRACT,
Line 22, delete "represehts" and insert -- represents --.
Line 23, delete "$SiO_2/Al_2\ O_3$" and insert -- $SiO_2/Al_2O_3$ --.

Signed and Sealed this

Thirtieth Day of November, 2004

JON W. DUDAS
*Director of the United States Patent and Trademark Office*